United States Patent [19]
Buckner, III et al.

[11] Patent Number: 5,348,185
[45] Date of Patent: Sep. 20, 1994

[54] CASSETTE FOR STERILIZING ARTICLES AND LATCH THEREFOR

[75] Inventors: Charles A. Buckner, III, Raleigh; Stephen B. Leonard, Fuguay-Varina, both of N.C.

[73] Assignee: American Sterilizer Company, Erie, Pa.

[21] Appl. No.: 40,668

[22] Filed: Mar. 31, 1993

Related U.S. Application Data

[62] Division of Ser. No. 851,487, Mar. 13, 1992, Pat. No. 5,234,124.

[51] Int. Cl.$^5$ .............................................. B65D 45/22
[52] U.S. Cl. .................................... 220/326; 220/378
[58] Field of Search ............... 220/326, 378, 254, 322, 220/356, 357, 358, DIG. 10, 315, 263

[56] References Cited

U.S. PATENT DOCUMENTS

| | | | |
|---|---|---|---|
| 2,776,778 | 1/1957 | Valvano | 220/326 |
| 3,101,154 | 8/1963 | Herdering | 220/326 |
| 3,147,880 | 9/1964 | Burman | 220/326 |
| 3,270,911 | 9/1966 | Sacks | 220/326 |
| 3,334,770 | 8/1967 | Stanback | 220/326 |
| 4,588,104 | 5/1986 | Danico | 220/326 |
| 5,065,885 | 11/1991 | Scaroni | 220/326 |

*Primary Examiner*—Joseph Man-Fu Moy
*Attorney, Agent, or Firm*—Jones, Day, Reavis & Pogue

[57] ABSTRACT

The invention relates to a container having first and second sections with at least one handle portion on each container facing each other in superimposed relationship to form a container and a latch mechanism associated with at least one handle for providing a preseal in the container by forcing the first and second sections toward each other in sealing arrangement and for maintaining the seal.

20 Claims, 6 Drawing Sheets

CASSETTE FOR STERILIZING ARTICLES AND LATCH THEREFOR

This is a division of application Ser. No. 07/851,487, filed Mar. 13, 1992, now U.S. Pat. No. 5,234,124.

FIELD OF THE INVENTION

The present invention relates generally to apparatus for sterilizing objects and in particular to a sealable cassette and latch therefor, the cassette containing the item to be sterilized through the introduction of sterilizing agents by means of input and output ports.

BACKGROUND OF THE INVENTION

Contamination by microorganisms is one of the most troublesome problems encountered today and there is often a need to sterilize devices such as medical instruments and the like.

In U.S. Pat. Nos. 4,169,123 and 4,169,124 methods are disclosed of cold gas sterilization using hydrogen peroxide gas of temperatures below 80° C. The liquid hydrogen peroxide is volatilized and the hydrogen peroxide vapor is then introduced into the sterilization chamber by air displacement.

U.S. Pat. No. 4,642,165 discloses a method of vaporizing successive increments of a multicomponent liquid such as an aqueous solution of hydrogen peroxide, for injection into a vacuum chamber. The vacuum in the chamber draws the multicomponent vapor into the chamber.

U.S. Pat. No. 4,512,951 discloses a method of liquid contact hydrogen peroxide sterilization. Goods to be sterilized are maintained in the sterilization chamber at a temperature below the dew point of the vapor sterilant. An aqueous solution of hydrogen peroxide is vaporized and passed into the evacuated sterilization chamber where, upon contact with the goods, the vapor condenses to form a liquid layer of sterilant on the goods. The vacuum in the chamber draws the vapor inside the chamber.

United Kingdom Patent No. 1,582,060 discloses a similar liquid contact hydrogen peroxide sterilization method operated without a vacuum chamber. Liquid hydrogen peroxide is pumped through an ultrasonic spray nozzle which is operated by a stream of dehydrated air. A mist of hydrogen peroxide is sprayed into a container and mixed with hot air to change the mist into a vapor. The vapor is piped into a nonpressurized sterilization chamber where it condenses on a cool moving web of material. A stream of hot air in an adjacent chamber removes the hydrogen peroxide layer from the web. The stream is then passed to a water separator where it is relieved of the sterilant.

In some other prior art systems, when the object such as a medical instrument has been sterilized, it must be removed from the sterilization chamber and handled in some form to be prepared for and transported to the medical facility for use. For instance, with the use of endoscopes which have multiple hollow tubes therein for air, water, vacuum and the like, the endoscope is placed in a container and input and output fluid connections are made to the appropriate endoscope connections and the chamber is sealed. A sterilizing fluid is introduced into the chamber where it not only surrounds and bathes the endoscope with the sterilizing agent, but is also passed through all of the hollow tubes of the endoscope by applying a vacuum on the other port, thus sterilizing the interior of any tubes.

However, the endoscope may still have moisture on it and the ambient air may then enter the chamber after the sterilization process or the endoscope may simply be removed from the chamber and placed in ambient air so that it will dry before use.

Such a system is inherently dangerous since any handling of the endoscope after sterilization or exposing it to ambient air after sterilization provides opportunity for recontamination of the endoscope. Further, it may continue to have moisture on the interior thereof which may contain contaminants that could be injected into the next patient with whom the endoscope is to be used.

These disadvantages of the prior art are overcome by the present invention which includes a sealable cassette in which the endoscope or other medical device is placed. The cassette has first and second fluid sealing ports for the introduction and removal of a sterilizing fluid. The endoscope or other medical instrument, if hollow, is coupled to the output port. The cassette is formed of two identical halves which are placed in superimposed sealable relationship with each other to form a hollow chamber. A latch is placed on one or more handles on the cassette to create a presealing condition to allow a vacuum to be introduced at the outlet port.

The cassette is then placed in an outer oven-like container or warming chamber where the temperature is properly maintained. Connections are made through the input and output ports on the cassette such that the sterilizing agent may be introduced through a first port to bathe the outside of the medical instrument or other object, such as an endoscope, while one end of the hollow object, such as the endoscope, is coupled to the output port where a vacuum is supplied external to the cassette to pull the sterilization agent inside the cassette through the interior passageways of the endoscope. When the sterilization process is completed, the warming chamber is opened and the sterilizing cassette is simply removed from the chamber with the input and output ports being uncoupled from their respective sources. A tight seal is maintained and the object remains in the sterilized interior of the cassette until the cassette is opened or the device is to be used. It can be stored, transported and handled without adversely affecting the sterilization of the object therein.

The cassette may have one or more handles for carrying it and a latch is utilized on at least one of the handles to preload the seals between the two cassette halves to enable a vacuum to be applied to the cassette when it is placed in the outer warming chamber. In the preferred-embodiment, one latch has a generally C-shaped portion having an arcuate section extending above, from the back of and curved toward the front of the C to form a handle for the latch. A projection on each end of the C generally faces each other and the projections are sufficiently spaced apart to engage a corresponding one of the handle portions to hold the handle portions of the cassette in a locked relationship with respect to each other. In one embodiment of the cassette that utilizes the C-shaped latch, a sloped shoulder is formed on each of the first and second handle portions such that the shoulders converge in a direction away from the cassette chamber. A trough or depression is formed on each cassette handle portion adjacent the highest portion of each slope such that as the C-shape body portion is pivoted from one handle portion toward the other, the projection on the upper outer end of the C-shape body portion engages and moves up the corresponding sloped shoulder of the handle and forces the sloped shoulders toward one another to seal the cassette. The upper outer end projection of the C engages the corresponding trough and locks the cassette halves together.

In the second embodiment, the latch is integrally formed and pivotally attached to the first handle portion. It has a generally horizontal leg for lifting the latch and a vertical leg with a projection thereon for latching contact with the second handle portion. A spring tab extends at an angle from the junction of the horizontal and vertical legs for releasably engaging the first handle portion. It releasably holds the vertical leg projection in positive latching contact with the second handle portion and flexes when the horizontal leg is lifted to release the latching contact of the vertical leg projection with the second handle portion to enable the cassette halves to be separated. In such case the respective handle portion in each cassette half includes an orifice in opposing relationship with the orifice in the opposing handle. A lip portion is formed in each of the first and second orifices. A horizontal projection at the bottom of the vertical leg provides latching engagement with the lip portion of the orifice in the second handle portion. The spring tab abuts the lip portion of the orifice in the first handle portion to provide a force to the vertical leg to hold the latch in positive latching contact with the lip portion in the orifice in the second handle portion. The spring tab is cantilevered and integrally formed with the horizontal and vertical legs of the catch. Thus by lifting up on the horizontal portion of the leg, the cantilevered spring tab is bent towards the vertical leg, thus allowing the vertical leg to move out of latching contact with the second handle portion and can be moved upwardly out of the orifice in both the first and second handle portions to allow the cassette halves to be separated.

Thus, it is an object of the present invention to provide a system for sterilizing a device and in particular a device such as a medical object as, for instance, an endoscope.

It is also an object of the present invention to provide a sealable cassette or container having a chamber in which the device to be sterilized can be placed, the chamber sealed, the cassette placed in an environmental control container, the device sterilized and the cassette removed from the container (where the proper temperature is maintained) and is kept in the sterilized condition inside the cassette until the next use of the device is required. No handling of the device to be sterilized is required after the device is placed in the cassette.

It is still another object of the present invention to provide a latch for the cassettes to maintain the cassettes in a sealable state to allow depressurization of the cassette for sterilization of the object therein and for maintaining the sealed relationship after the sterilization process is completed to prevent the object therein from being recontaminated.

It is still another object of the present invention to provide a sterility guard to indicate the possibility of a container having been opened if the guard has been removed.

SUMMARY OF THE INVENTION

Thus, the present invention relates to a sterilization cassette having first and second identical halves in sealed relationship with at least one handle portion on each cassette half facing each other in superimposed relationship to form a cassette handle with first and second handle portions.

An input and an output port is provided in the cassette to enable a sterilizing fluid to be introduced into the interior of the cassette in one port and removed from the cassette through the other port. A seal is placed between the two cassette halves extending around the periphery of the interior thereof, and a latch mechanism is associated with at least one handle for providing a preseal in the cassette by forcing the first and second said halves toward each other in sealing arrangement and for maintaining the seal after the sterilization process has been completed.

The invention also relates to a latch for a sterilization cassette that has first and second halves each with at least one handle portion facing the other in superimposed relationship to form a cassette handle with first and second handle portions and wherein the latch comprises an integrally formed catch for pivotal attachment to the first handle portion and having a generally horizontal leg for lifting and a vertical leg with a projection thereon for latching contact with a second handle portion, a spring tab extending at an angle from the junction of the horizontal and vertical legs for releasably engaging the first handle portion so as to releasably hold the vertical leg projection in positive latching contact with the second handle portion and which flexes when the horizontal leg is lifted to release the latching contact of the vertical leg projection with the second handle portion to enable the cassette to be separated into its two halves. The cassette in such case has first and second opposing orifices in the respective handle portions, a lip portion in each of the first and second orifices, a horizontal projection at the bottom of the vertical leg for latching engagement with the lip portion of the orifice in the second handle portion and a spring tab abutting the lip portion in the orifice of the first handle portion to provide a force to the vertical leg to hold the latch in positive latching contact with the lip portion in the orifice of the second handle portion.

The invention also relates to an alternative latch embodiment to close the sterilization cassette comprising a generally C-shaped body portion having an arcuate section extending above, from the the back of and curved toward the front of the C to form a handle for the latch and a projection on each end of the C generally facing each other, the projections being sufficiently spaced apart to engage a corresponding one of the first and second handle portions to hold the handle portions of the cassette in a locking relationship to each other. In such case, a sloped shoulder is formed on the first and second handle portions such that the shoulders are converging in a direction away from the cassette chamber. A trough or recession is formed on each cassette handle portion adjacent the highest point in the sloping shoulder such that as the C-shaped body portion is pivoted from one handle portion toward the other, the projection on the upper outer C-shaped body portion engages and moves up the corresponding sloped shoulder to force the sloped shoulders toward each other to seal the cassette, the projection on the upper outer end engaging the corresponding trough and locking the cassette halves together.

BRIEF DESCRIPTION OF THE DRAWINGS

These and other objects of the present invention will be more fully disclosed in conjunction with the following detailed description of the drawings in which like numerals represent like elements and in which.

DETAILED DESCRIPTION OF THE DRAWINGS

Figure 1:
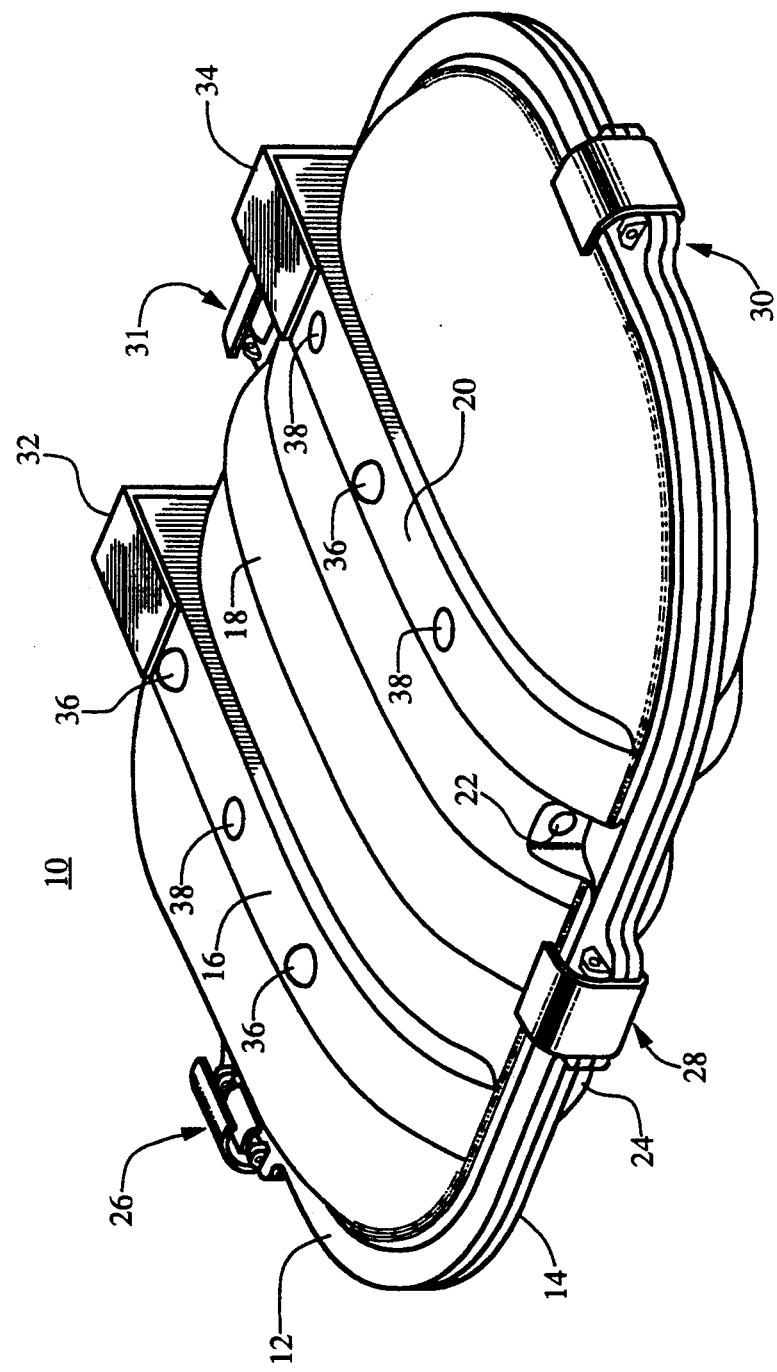
FIG. 1 is an isometric view of one embodiment of a cassette of the present invention.

One embodiment of the novel cassette of the present invention is shown in FIG. 1. A cassette 10 includes identically formed upper and lower halves 12 and 14 forming a hollow chamber. Each half has strengthening ribs 16, 18 and 20 extending from one side with handles 26, 28, 30 and 31 thereon. The side with handle 28 could be called the top and the opposing side with handle 31 could be called the bottom. A fluid input port 22 is formed in the upper half 12 of the cassette 10 while a corresponding fluid outlet port 24 is formed in the bottom half 14 of the cassette 10. The input and output ports could be reversed as far as fluid flow is concerned. Handles 26, 28 and 30 are formed on at least three sides of the cassette 10. Handle 31 may be added if desired. Also, if desired, molded feet 32 could be provided having rubber inserts attached thereto in any well-known manner so that the cassette 10 can be stood on end such as a briefcase and the rubber feet would protect the bottom of the cassette 10 in such case. If desired, the molded feet 32 and 34 may be omitted. Registration tabs 36 and 38 may be molded on the ribs 16 and 20 to allow multiple cassettes to stack neatly. If desired, an insert (not shown) may be placed substantially at the center of the cassette on the interior thereof which extends from one side of the hollow chamber to the other and essentially engages both cassette halves. This insert is important when the unit has a vacuum applied thereto to prevent the sides 12 and 14 of the cassette 10 from moving towards each other sufficient to collapse the chamber.

Figure 2:
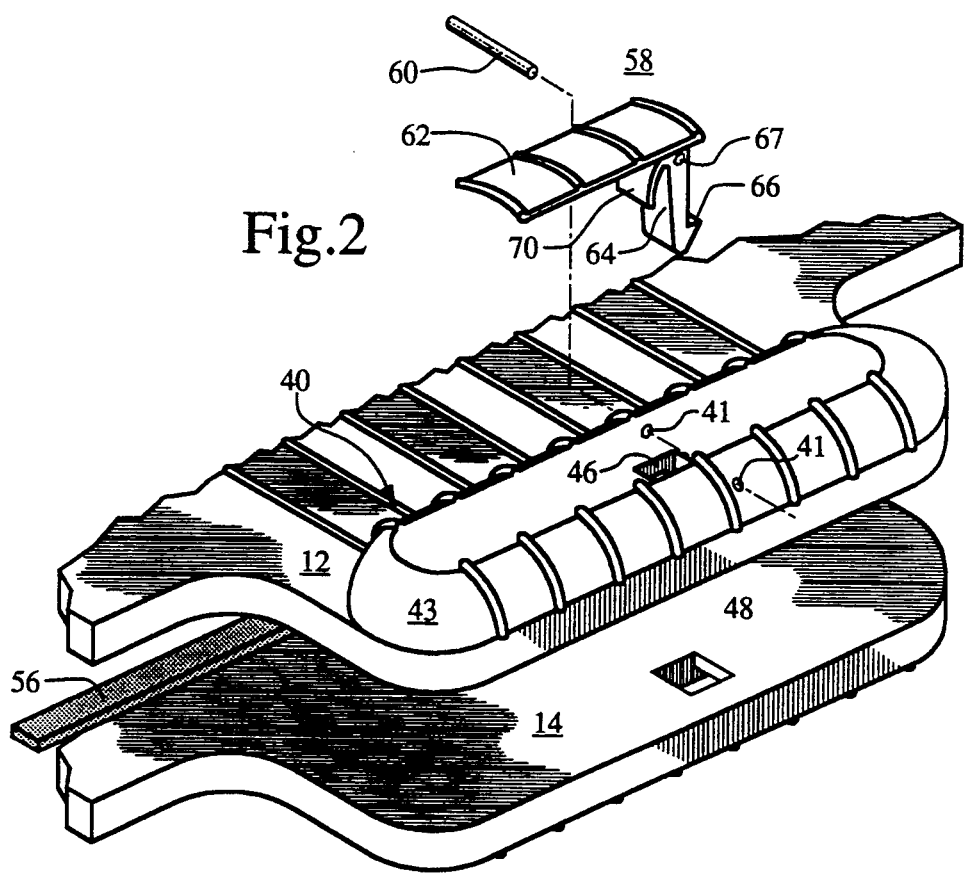
FIG. 2 is a partial isometric exploded view of the handle portion of the cassette of FIG. 1 illustrating the latch, the handle arrangements and the manner in which the latch is pivotally attached to the handle.

An exploded view of one of the handle portions of the cassette 10 is illustrated in FIG. 2. Since the cassette 10 is formed of identical halves 12 and 14, the bottom side of the handle on the half 14 in FIG. 2, which cannot be seen, is identical to the handle portion illustrated on cassette half 12. Thus, cassette half 12 has raised handle portion 40 and cassette half 14 has raised handle portion 42, shown clearly in FIG. 3. Handle 40 has an orifice 46 formed therein and handle 42 has an orifice 48 formed therein. A latch 58 is an integrally formed catch for pivotal attachment about pin 60 in the handle 40 through orifices 41. The catch 58 has a generally horizontal leg 62 for lifting and a vertical leg 64 with a projection 66 thereon for latching contact with the second handle portion 14. A spring tab 70 extends at an angle from the junction of the horizontal and vertical legs 62 and 64, respectively, for releasably engaging the first handle portion 40 so as to releasably hold the vertical leg projection 66 in positive latching contact with the second handle portion 14. The spring tab 70 flexes when the horizontal leg 62 is lifted to release the latching contact of the vertical leg portion 64 with the second handle portion 14 to enable the cassette halves to be separated.

Figure 3:
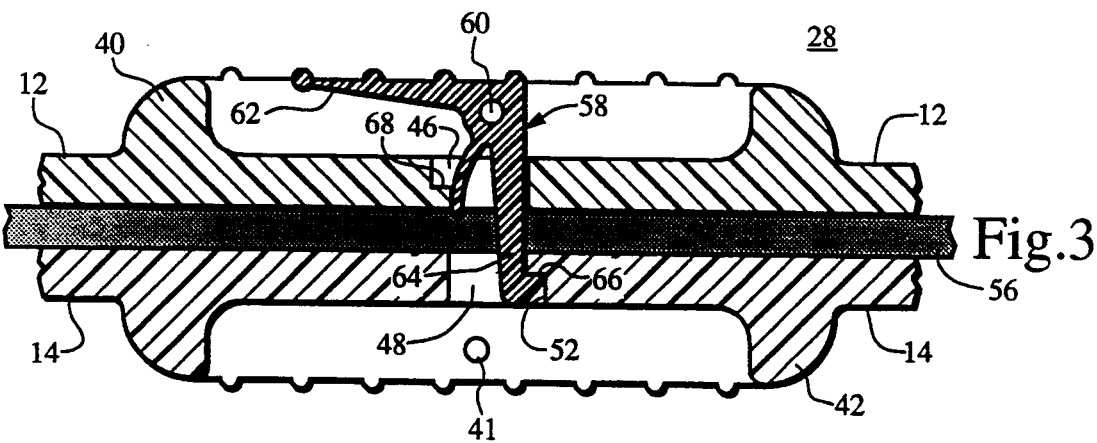
FIG. 3 is a cross-sectional view of the handle and latch portion illustrating the manner in which the latch holds the cassette halves in sealing arrangement with each other.

FIG. 3 is a cross-sectional view of the handle in FIG. 2 with the latch 58 holding the two cassette halves 12 and 14 in sealing relationship with each other with seal 56 between them. It can be seen in FIG. 3 that the first and second orifices 46 and 48 are in substantially opposing relationship in the respective handle portions 12 and 14. A lip portion 68 is formed in each of the first and second orifices 46 and 48. A horizontal projection 66 is formed at the bottom of the vertical leg 64 for latching engagement with the lip portion 68 of the orifice 48 in the second handle portion 14. The spring tab 70 abuts the lip portion edge 50 of orifice 46 in the first handle portion 40 to provide a force to the vertical leg 64 to hold the latch 58 in positive latching contact with the lip portion 68 in the orifice 48 of the second handle portion 14. Because the handles 40 and 42 and the entire cassette halves 12 and 14 are identical to each other, the latch 58 could be inserted from either side. Oval shaped surface 43 projects outwardly from handle portion 40 and orifice 41 is formed in each handle portion projecting surface 40 and 42 in a horizontal plane. An orifice 67 is formed in the latch 58 substantially at the junction of the horizontal and vertical legs 62 and 64, respectively. A pin 60 extends through the latch orifice 67 and the first handle portion projecting surface orifice 41 for pivotally attaching the catch 58 to the first handle portion 40. As indicated previously, the first and second handles or handle portions 40 and 42 are identically constructed such that the catch 58 may be pivotally attached to either the first or second handle portion 40 or 42.

Figure 4:
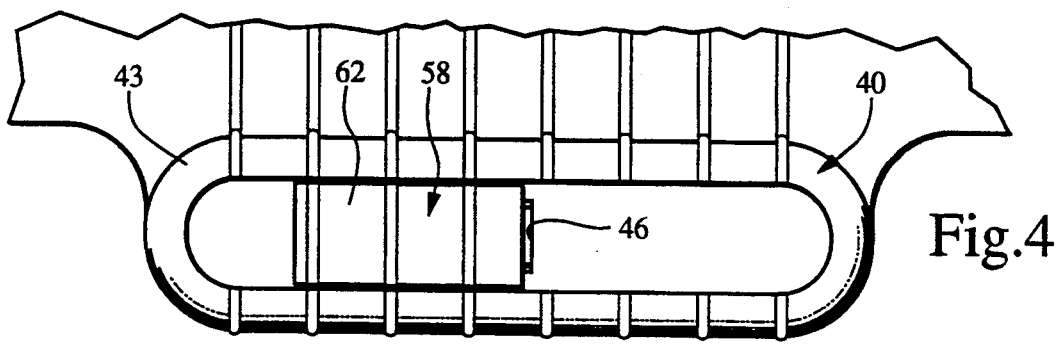
FIG. 4 is a top view of the handle portion of one of the handles of the cassette.

FIG. 4 is a top view of the handle 40 illustrating the oval-shaped projecting surface 43 and the catch 58 inserted in orifice 46 such that the horizontal portion 62 of the latch 58 can be lifted upwardly to pivot the vertical leg 64 away from the latching contact with the bottom handle raised portion 42.

Figure 5:
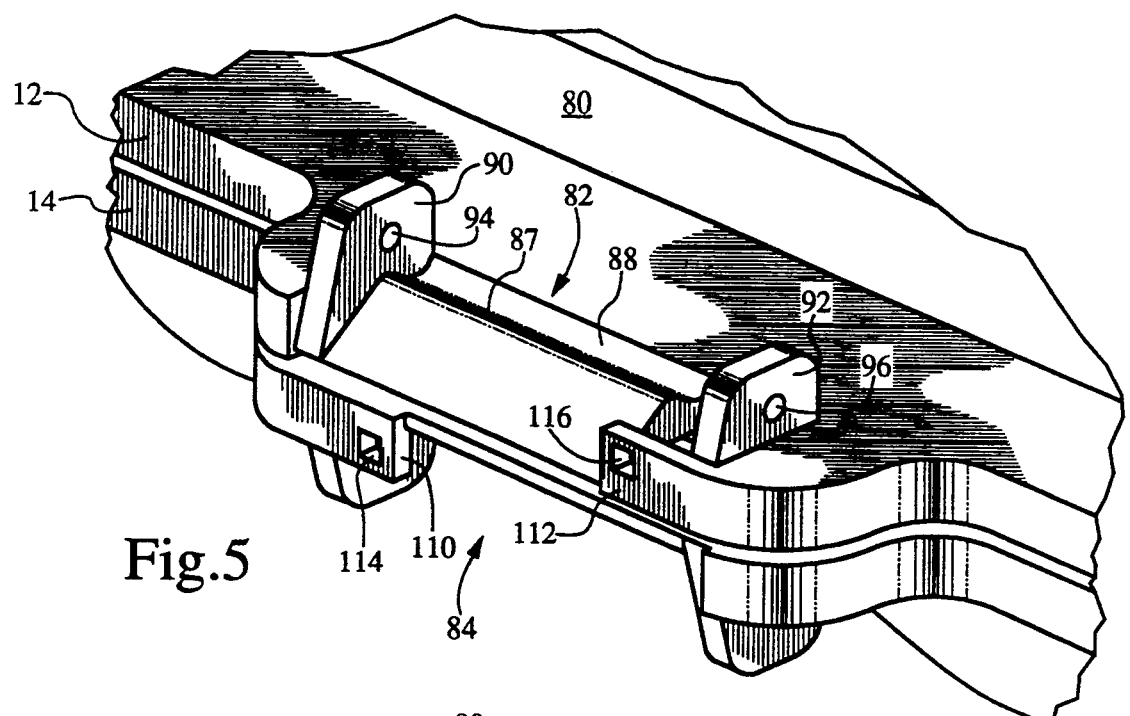
FIG. 5 is a partial isometric view of one of the handles of the cassette for use with the alternate latch of FIGS. 6A and 6B.

A second embodiment of the cassette handle is illustrated in FIG. 5. The remainder of the cassette, except for the handles, is identical to that disclosed in FIG. 1 of the present invention. In FIG. 5, the handle 80 is composed of first and second identical handle portions 82 and 84 in superimposed relationship. As disclosed in FIG. 5, first and second identical cassette halves 12 and 14 have at least one handle 80 rigidly formed in the cassette, handle 80 being formed of first and second identical handle portions 82 and 84 in superimposed relationship with each other as shown. Because the handle portions 82 and 84 are identical in construction, only handle portion 82 will be disclosed in detail. Where necessary, as in FIG. 6A, corresponding elements on handle portion 84 are designated by a prime such as 86'. Handle portion 84 would look exactly like handle portion 82 if the cassette were turned over so that handle portion 84 was on top in FIG. 5 and handle portion 82 was on the bottom. Handle portion 82 has a sloped shoulder 86 thereon such that it would converge with the same sloping portion of second handle portion 84 in a direction away from the cassette chamber toward the outer edge of the cassette. A shallow trough 88 is formed adjacent the highest point 87 of the slope 86. First and second identical spaced projections 90 and 92 on handle portion 82 have orifices 94 and 96, respectively, therein for receiving a body portion of a handle therebetween.

Figure 6A:
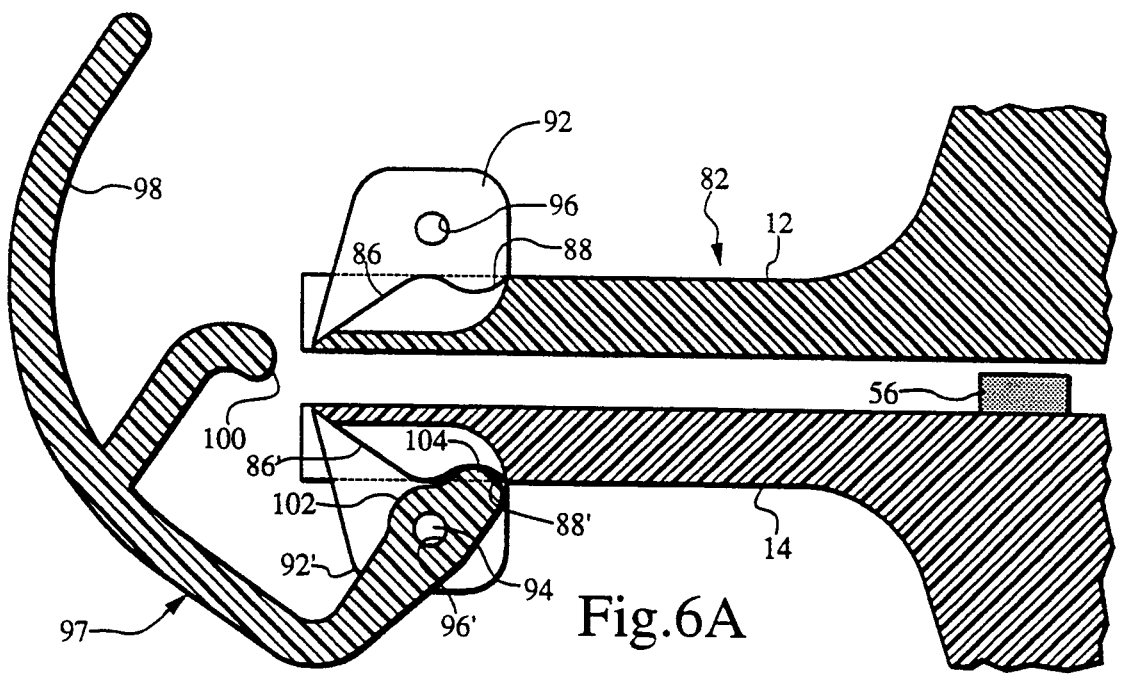
FIG. 6A is a view of an alternate latching mechanism for the cassette handle of FIG. 5 with the latch in the open position.
Figure 6B:
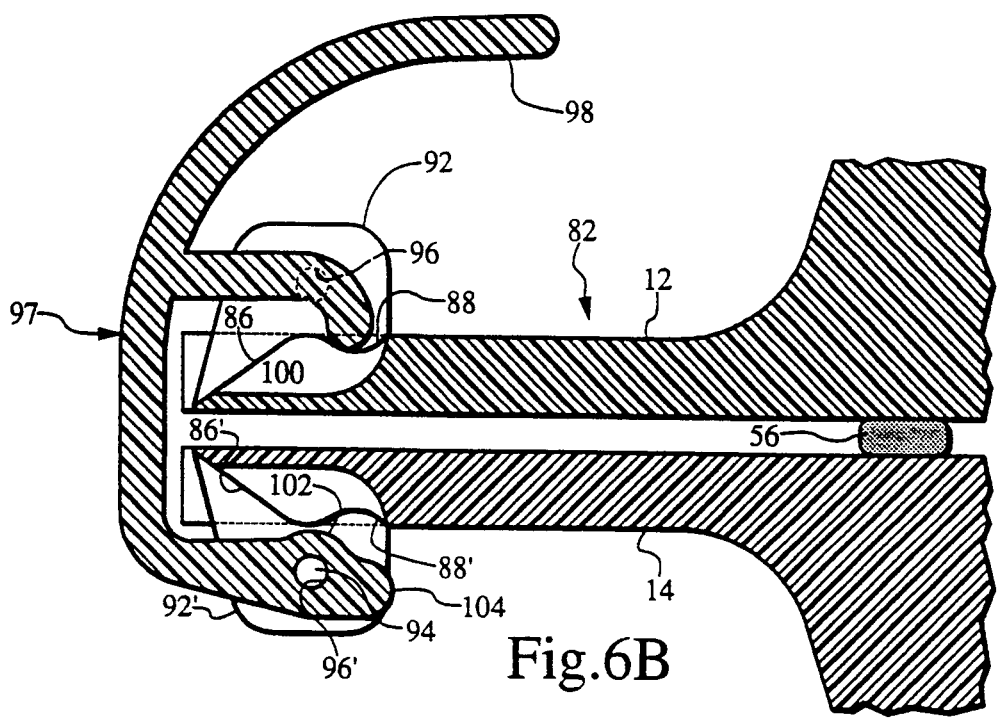
FIG. 6B is a partial view of the alternate latching mechanism for the cassette handle of FIG. 5 with the latch in the closed position.

A cross-sectional view of one of the handles is illustrated in FIGS. 6A and 6B. In FIG. 6A the handle is in the opened position. The handle includes a generally C-shaped body portion 97 having an arcuate section 98 extending above, from the back of and curved toward the front of the C-shaped body 97 to form a latch for the cassette. Spaced projections 100 and 102 on the respective ends of the C-shaped body 97 generally face each other, the projections being sufficiently spaced apart to engage corresponding ones of the first and second handle portions 82 and 84 to hold the first and second handle portions 82 and 84 of the cassette in a locking relationship to each other. An orifice 96' in the lower spaced projection 92' is in alignment with an orifice 91 (see FIG. 8) that extends lengthwise in the lower outer end of the C-shaped body portion 97 in axial alignment with and between the orifices 94' and 96' on the first and second spaced projections 90' and 92'. A pin 104 is inserted through the spaced projection orifices 94' and 96' and the C-shaped body portion orifice 91 to pivotally attach the C-shaped body portion 97 to the handle 80.

As can be seen in FIG. 6B, as the C-shaped body portion 97 is pivoted from the position shown in FIG. 6A to the position shown in 6B, it moves toward the slope 86 such that the upper outer end 100 of the C-shaped body portion 56 engages and moves up the sloped shoulder 86 and forces the handle portion 82 toward the other handle portion 84 to compress seal 56 and seal the cassette. The upper outer end projection 100 passes over the highest point 87 of the slope and engages the corresponding trough 88 to lock the cassette halves together. At that time, the seal 56 is compressed and, thus, the cassette halves are locked together in sealing relationship.

Figure 7:
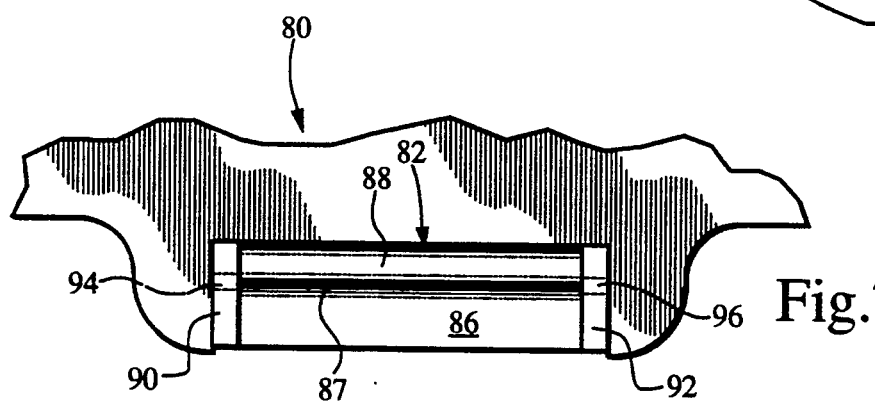
FIG. 7 is a top view of the handle portion illustrated in FIG. 5.

FIG. 7 is a top view of the handle portion 82 of the handle 80. It has the sloping shoulder 86, the groove 88 adjacent the highest point 87 of the slope 86 and the spaced vertical projections 90 and 92 with the respective orifices 94 and 96 therein.

Figure 8:
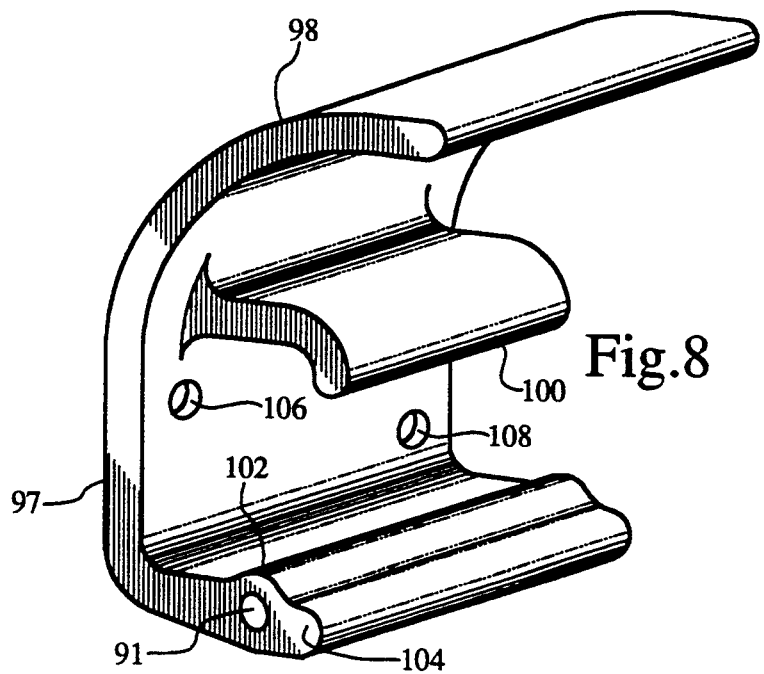
FIG. 8 is an isometric view of the latching mechanism for the alternate handle of FIG. 5.

FIG. 8 is an isometric view of the novel C-shaped latch. It can be seen in FIG. 8 that the C-shaped body portion 97 is elongated in width. It is also noted that the upper projection 100 on the upper end of the C-shaped body portion 97 is shorter in width than the elongated width of the remainder of the body portion 97. Projection 104 on the lower outer end of the C-shaped body portion 97 provides a stop position for the C-shaped body portion 97 when the handle is in the opened position as illustrated in FIG. 6A. At that point, the outer projection 104 engages depression 88', thus preventing the C-shaped body portion 97 from rotating further in a counterclockwise direction. This prevents the handle from dropping down completely when the cassette halves are not attached together. The C-shaped body portion 97 also includes orifices 106 and 108 for a sterility tab as will be discussed hereafter in relation to FIG. 10.

Figure 9:
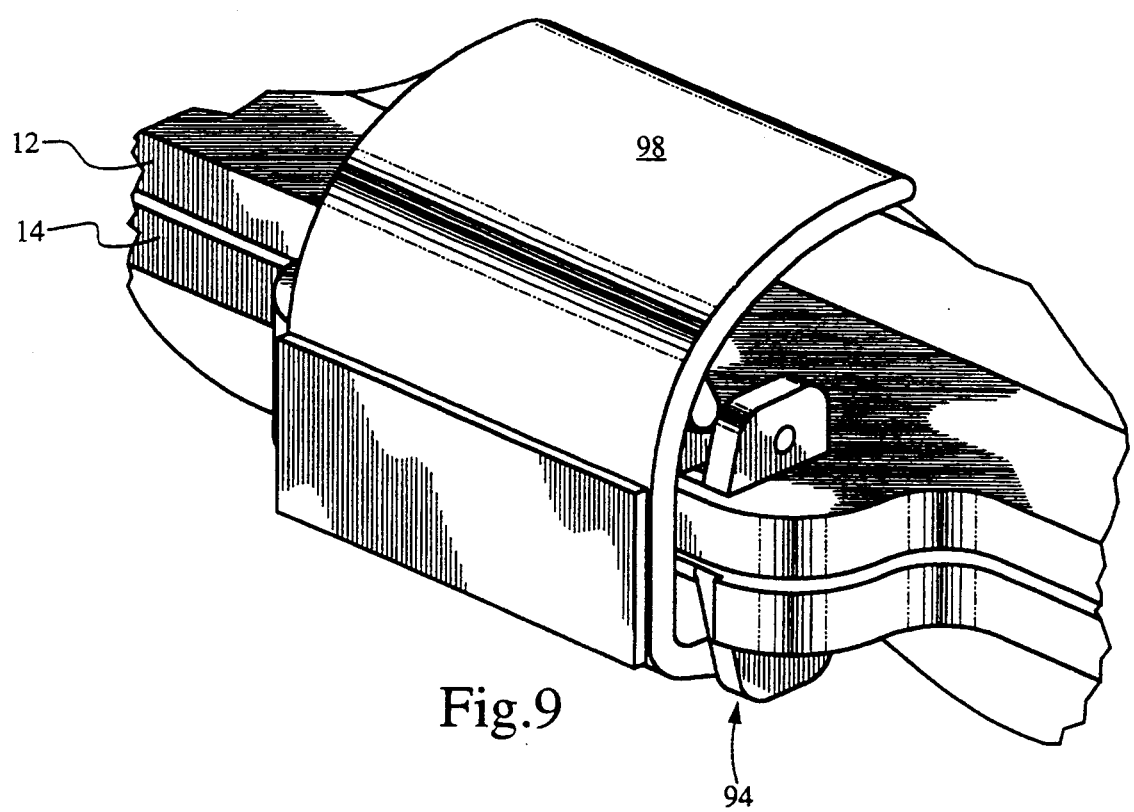
FIG. 9 is a partial isometric view of the latch of the alternate embodiment in use with the handle in FIG. 6 illustrating both of the opposing handle portions held in abutting relationship with each other by the latch.

FIG. 9 is a perspective view illustrating the C-shaped handle mounted on the lower handle portion 94 and in the closed position sealingly latching the upper cassette half 12 with the lower cassette half 14.

Figure 10:
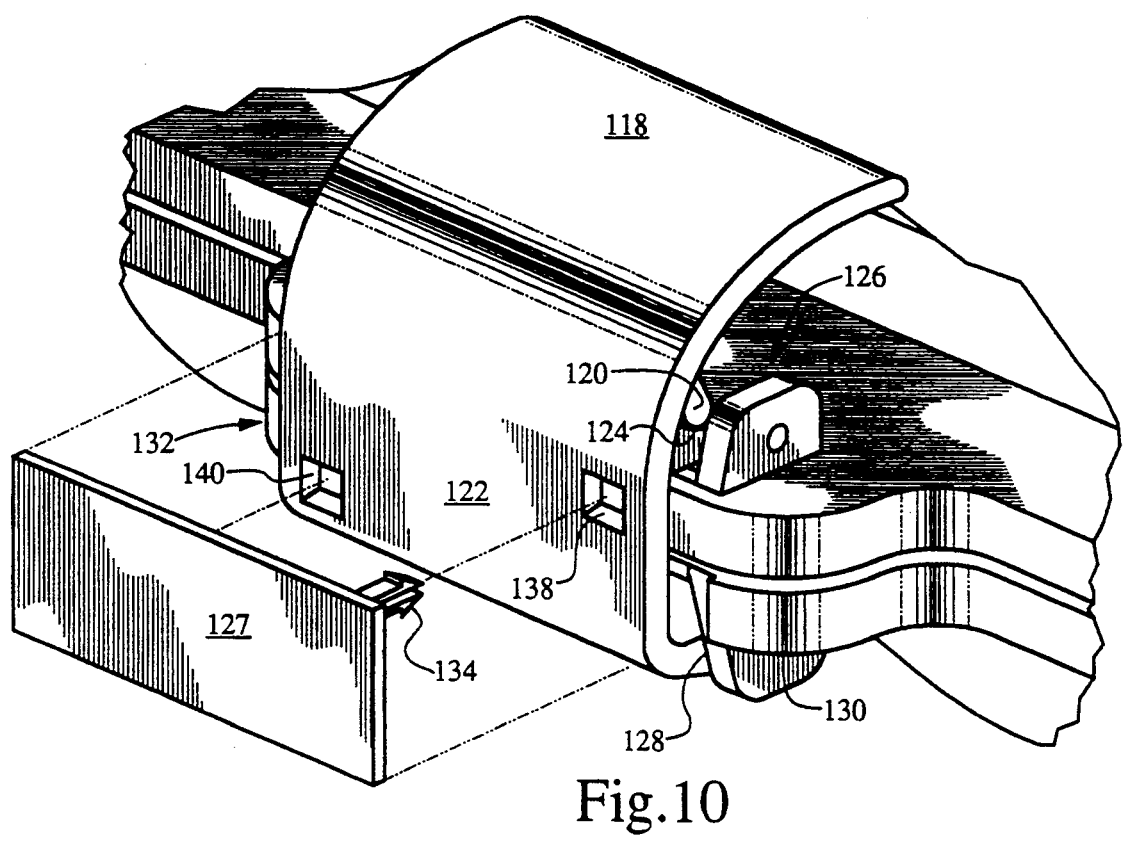
FIG. 10 is a partial isometric view of the handle of the alternate embodiment illustrated in FIG. 5 in which the latch is shown in the closed position and a sterility guard or indicator is shown which provides a visual indication if the latch has possibly been opened and the sterility of the cassette been compromised.
Figure 11:
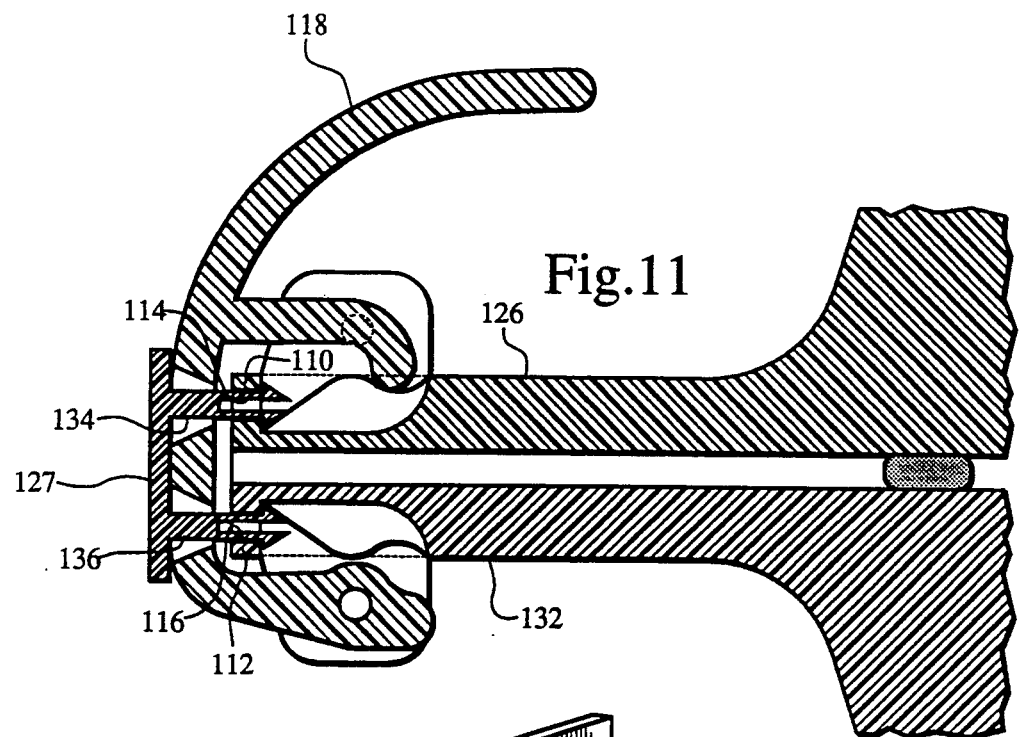
FIG. 11 is a cross-sectional view of the sterility guard in place.

If it is desired to place a sterility guard or tab on the device, it can be done as illustrated in FIGS. 10 and 11 wherein a C-shaped latch 118 is shown with the outer end 120 of the upper portion of the C-shaped body 122 engaging the recess 124 in the upper half 126 of the handle. In like manner, the lower projection 128 of the C-shaped body portion 122 is pivotally attached at 130 to the lower half 132 of the cassette handle. A plate 127 has projections 134 and 136 (FIG. 12) extending through corresponding orifices 138 and 140 (106 and 108 in FIG. 8) of the C-shaped portion 122. They also extend to orifices 114 and 116, respectively, (see FIG. 11) of vertical projections 110 and 112 on the upper and lower cassette handle halves 126 and 132, respectively (see FIG. 11). The projections 134 and 136 are made of frangible material and thus when handle 118 is attempted to be pulled downwardly about pivot point 130, the projections 134 and 136 shatter, thus releasing plate 127. Thus an indication is given that the sterility of the cassette assembly may have been violated.

Figure 12:
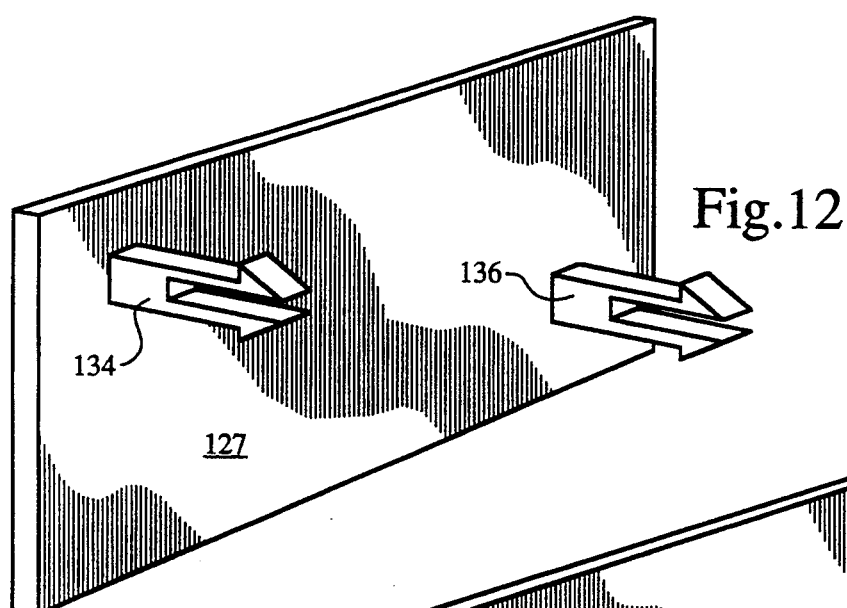
FIG. 12 is an isometric view of the plate used as the sterility guard in FIG. 11.
Figure 13:
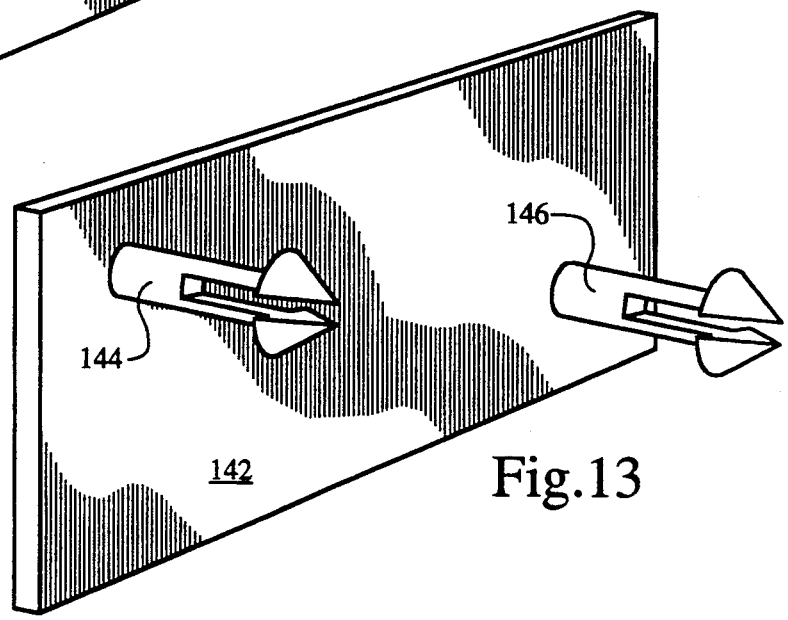
FIG. 13 is an isometric view of an alternate plate used as the sterility guard for attaching to the C-shaped handle and cassette.

FIG. 12 illustrates that the projections 134 and 136 may be rectangular in cross section while FIG. 13 illustrates that they may be circular in cross section as indicated by projections 144 and 146.

Thus, there has been disclosed a novel cassette and system for sterilizing objects therein. The object may be placed within the cassette halves, the halves sealed together with a latch arrangement, the cassette placed in an environmentally controlled container with fluid input and fluid output sources coupled to input and output ports, respectively, on the cassette. The output (or input) port of the cassette may be coupled to a hollow device inside the cassette such that the sterilizing fluids not only surround and bathe the device within the cassette, but also during the vacuum process the sterilizing fluid is passed through the internal lumens of the device so that the device can be sterilized both inside and outside. The fluid sources are disconnected from the cassette and the cassette with the sterilized device therein may simply be stored or stacked until it is needed to be used. Because the latching arrangements keep the cassette in a sealed condition, the device therein cannot be recontaminated from the outside.

To keep the cassette in a sealed condition, a latch is used on at least one handle and preferably two latches are used, one on opposing sides, to maintain a seal between the two cassette halves. In one latching arrangement, opposing orifices are formed in the opposing handle portions that are in superimposed relationship to form an entire handle. A latch assembly is inserted through the two orifices with a vertical leg assembly. A horizontal leg is integrally formed with the vertical leg and is pivotally attached at the junction thereof to the upper handle portion. A cantilevered spring tab is integrally formed with the horizontal and vertical legs of the catch and press against the lip found in the orifice of the top handle portion. The lower portion of the vertical leg also has a horizontal projection which engages a corresponding lip in the orifice in the bottom handle portion of the cassette. The latch is pivotally attached to the upper handle by means of a pin that passes through orifices in the upper handle portion and the latch. By lifting up on the horizontal portion of the latch, the cantilevered tab or spring tab is compressed, thus allowing the vertical leg to move the horizontal projection thereon out of locking engagement with the lip in the orifice in the lower handle portion, thus unlatching the two cassette halves.

In another embodiment, the upper and lower handle portions have sloping shoulders thereon that converge towards the outer edge of the cassette. A groove or depression is formed adjacent the highest point of the sloping shoulders and a C-shaped clamp is pivotally attached to the lower handle portion such that the upper portion of the C, when the handle is closed, slides up the ramp of the upper handle portion forcing it downwardly toward the bottom portion, thus sealing the first and second cassette halves together. When the outer end of the upper portion of the C-shaped body passes over the highest point of the slope, it drops into the depression thus locking itself to the first and second cassette halves and locking the halves together in sealing relationship.

While in the foregoing we have disclosed embodiments of the invention in considerable detail for purposes of illustration, it will be understood by those skilled in the art that many of these details may be varied without departing from the spirit and scope of the invention.

We claim:

1. A latch to close a container, the container having first and second sections with at least one handle portion on one container section facing the other in superimposed relationship to form a container handle with first and second handle portions, the latch comprising:
    a generally C-shaped body portion having an arcuate section extending above, from the back of and curved toward the front of the C to form a grip for the latch; and
    a spaced projection on each end of the C generally facing each other, the projections being sufficiently spaced apart to engage a corresponding one of first and second handle portions to hold the first and second container sections in a latched relationship to each other.

2. A latch as in claim 1 further comprising an orifice extending lengthwise in the outer end of the C-shaped body portion for pivotally attaching the C-shaped body portion to the container.

3. A latch as in claim 2 wherein the C-shaped body portion is elongated.

4. A latch as in claim 3 further including a sealing element around the periphery of the container between the first and second sections to form a fluid-tight seal when the latch is closed.

5. A container for holding an object in a fluid-tight chamber comprising:
    first and second container sections;
    at least one handle rigidly formed in the container, the handle being formed of first and second identical handle portions in superimposed relationship;
    a generally C-shaped latch for holding the two sections of the container together, the latch having an arcuate section extending above, from the back of and curved toward the front of the C to form a grip for the latch; and
    a projection on each end of the C generally facing each other, the projections being sufficiently spaced apart to engage a corresponding one of the first and second handle portions to hold the first and second handle portions of the container in a locking relationship to each other.

6. A container as in claim 5 further including:
    first and second identical spaced vertical projections on each of the first and second handle portions for receiving the C-shaped latch therebetween;
    an orifice in each first and second spaced projections in axial alignment;
    an orifice extending lengthwise in the lower outer end of the C-shaped latch for axial alignment with and between orifices in the first and second spaced projections; and
    a pin for insertion through the C-shaped latch orifice and the spaced projection orifices to pivotally attach the C-shaped latch to the handle.

7. A container as in claim 6 further including:
    a sloped shoulder on each of the first and second handle portions such that the shoulders are converging in a direction away from the container chamber; and
    a depression on each cassette handle portion adjacent the highest point of each handle portion slope such that as the C-shaped latch is pivoted from one handle portion toward the other, the projection on the upper outer end of the C-shaped latch engages and moves up the corresponding sloped shoulder and forces the sloped shoulders toward each other to seal the container, the upper outer end projection engaging the corresponding depression and locking the container sections together.

8. A container as in claim 7 further including a sealing element around the periphery of the container between the first and second sections to form a fluid-tight seal when the container latch is closed.

9. A container as in claim 5 further including a guard attached to the C-shaped latch and the container to indicate possible opening of the container if the guard has been removed.

10. A container as in claim 9 wherein the guard comprises:
    at least one orifice extending through the back of the C - shaped latch;
    at least one orifice in the container aligned with the orifice in the C-shaped latch;
    a plate having at least one frangible pin thereon for insertion in the aligned orifices; and
    locking ends on the pin for latchingly engaging the container such that the frangible pin must be broken to pivot the C-shaped latch to open the container thereby indicating a possible opening of the container.

11. A container as in claim 5 wherein the container sections are identical halves having a plurality of opposing handle portions each of which is held together by one of said C-shaped latches.

12. A latch for a container having first and second sections and at least one handle portion on each container section facing each other in superimposed relationship to form a container handle with first and second handle portions, the latch comprising:

an integrally formed catch for pivotal attachment to the first handle portion and having a generally horizontal leg for lifting and a vertical leg with a projection for latching contact with the second handle portion; and a spring tab extending at an angle from the junction of the horizontal and vertical legs for releasably engaging the first handle portion so as to releasably hold the vertical leg projection in positive latching contact with the second handle portion and which flexes when the horizontal leg is lifted to release the latching contact of the vertical leg projection with the second handle portion to enable the container sections to be separated.

13. A latch as in claim 12 further including an orifice in the latch for pivotally attaching the latch to the container.

14. A container having first and second sections held together by at least one latch and comprising:

at least one handle portion on each container section facing each other in superimposed relationship to form a container handle with first and second handle portions;

an integrally formed catch for pivotal attachment with the first handle portion and having a generally horizontal leg for lifting and a vertical leg with a projection for latching contact with the second handle portion; and a spring tab extending at an angle from the junction of the horizontal leg and the vertical leg for releasably engaging the first handle portion to provide a force to releasably hold the vertical leg projection in positive latching contact with the second handle portion and which flexes when the horizontal leg is lifted to release latching contact of the vertical leg projection with the second handle portion to enable the container sections to be separated.

15. A container as in claim 14 further including an orifice in the latch and container handle for pivotally attaching the latch to the container.

16. A container as in claim 15 further comprising:

an oval shaped surface projecting outwardly from each of the superimposed handle portions;

an orifice in each handle portion projecting surface;

an orifice in the catch substantially at the junction of the horizontal and vertical legs; and a pin extending through the latch orifice and the first handle portion projecting surface orifice for pivotally attaching the catch to the first handle portion.

17. A container as in claim 16 wherein the first and second handles are identically constructed such that the catch may be pivotally attached to either the first or second handle portions.

18. A container as in claim 17 wherein a spring tab is a cantilevered tab integrally formed with the horizontal and vertical legs of the latch.

19. A container as in claim 18 further including a sealing element around the periphery of the container between the first and second sections to form a fluid-tight seal when the container latch is closed.

20. A container as in claim 14 wherein the container sections are identical halves having a plurality of opposing handle portions each of which is held together by one of said latches.

* * * * *